United States Patent
Makdissi

(10) Patent No.: US 8,359,089 B2
(45) Date of Patent: Jan. 22, 2013

(54) RECONSTRUCTION OF A SURFACE ELECTROCARDIOGRAM FROM FAR FIELD SIGNALS EXTRACTED OF AN ENDOCARDIAL ELECTROGRAM

(75) Inventor: Alaa Makdissi, Paris (FR)

(73) Assignee: Sorin CRM S.A.S., Clamart (FR)

( * ) Notice: Subject to any disclaimer, the term of this patent is extended or adjusted under 35 U.S.C. 154(b) by 190 days.

(21) Appl. No.: 12/755,224

(22) Filed: Apr. 6, 2010

(65) Prior Publication Data
US 2010/0256699 A1    Oct. 7, 2010

(30) Foreign Application Priority Data
Apr. 6, 2009    (FR) ...................................... 09 01661

(51) Int. Cl.
*A61B 5/0402*    (2006.01)
(52) U.S. Cl. ............................ 600/509; 600/510; 607/32
(58) Field of Classification Search .................. 600/509, 600/510; 607/32
See application file for complete search history.

(56) References Cited

U.S. PATENT DOCUMENTS

| | | | |
|---|---|---|---|
| 5,740,811 A | 4/1998 | Hedberg et al. | |
| 6,980,850 B1 | 12/2005 | Kroll et al. | |
| 7,349,732 B1 | 3/2008 | Kil et al. | |
| 7,383,080 B1 | 6/2008 | Kil et al. | |
| 2008/0065161 A1 | 3/2008 | Lian et al. | |
| 2008/0114257 A1 | 5/2008 | Molin et al. | |
| 2008/0114259 A1 | 5/2008 | Molin et al. | |

FOREIGN PATENT DOCUMENTS

| EP | 1897587 | 3/2008 |
|---|---|---|
| EP | 1902750 | 3/2008 |

OTHER PUBLICATIONS

Foreign Search Report (Annexe Au Rapport De Recherche Preliminaire Relatif A La Demande De Brevet Francais No. FR09016611 FA 720220).

*Primary Examiner* — Joseph Dietrich
(74) *Attorney, Agent, or Firm* — Orrick Herrington & Sutcliffe, LLP

(57) ABSTRACT

Reconstruction of a surface electrocardiogram from far field signals extracted from an endocardial electrogram in an active medical device is disclosed. The device collects a ventricular EGM signal ($EGM_V$) and an atrial EGM signal ($EGM_A$), and extracts a ventricular far field signal component ($FF_V$) and an atrial far field signal component ($FF_A$). The ventricular and atrial far field signal components are combined to deliver as an output a reconstructed surface electrogram ECG signal ($ECGj^*$). The ventricular and atrial far field signals are respectively extracted from the collected ventricular and atrial EGM signals ($FF_V$, $FF_A$). The reconstruction of the ECG is operated by ventricular (18) and atrial (16) far field signal estimator filters. According to one embodiment, the far field signal estimator filters are linear or nonlinear filters, receiving as input the far field signal components. An adder (20) adds the filtered signals and delivers as output the reconstructed ECG signal ($ECGj^*$).

22 Claims, 2 Drawing Sheets

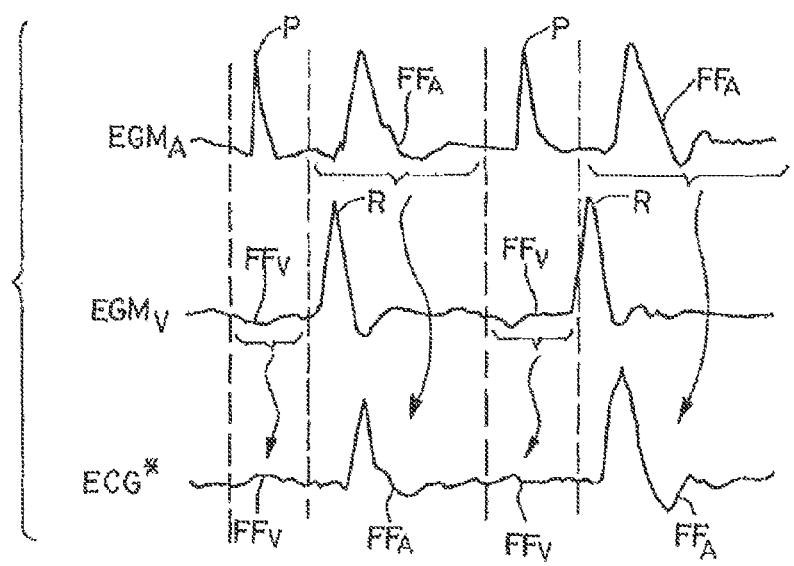
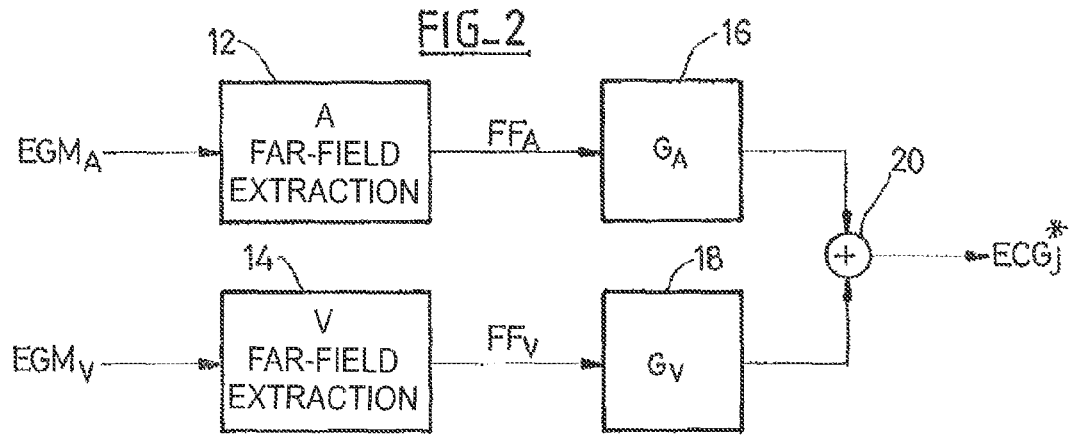
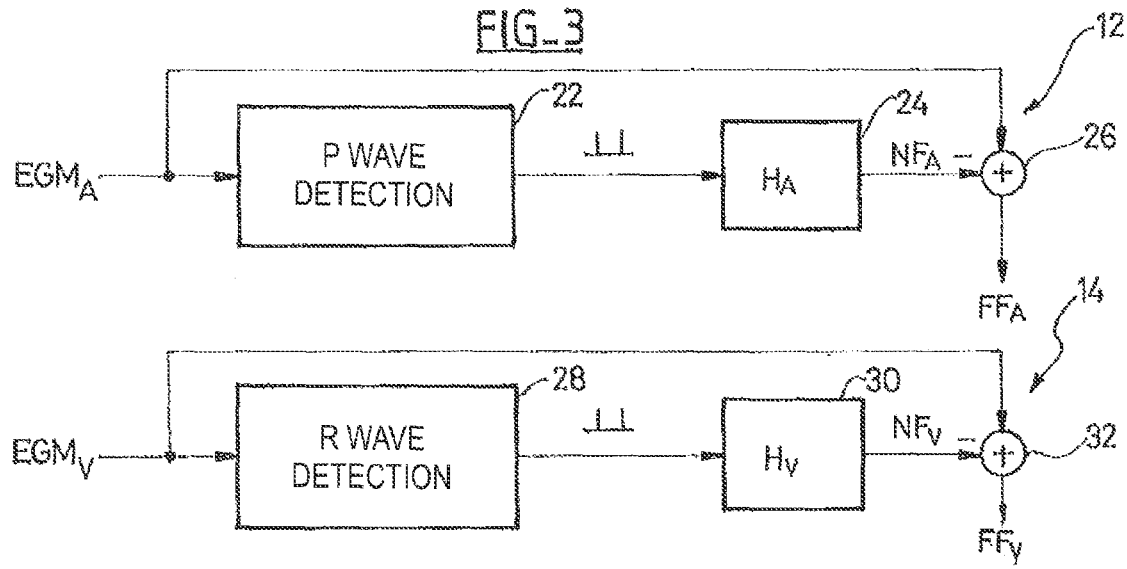

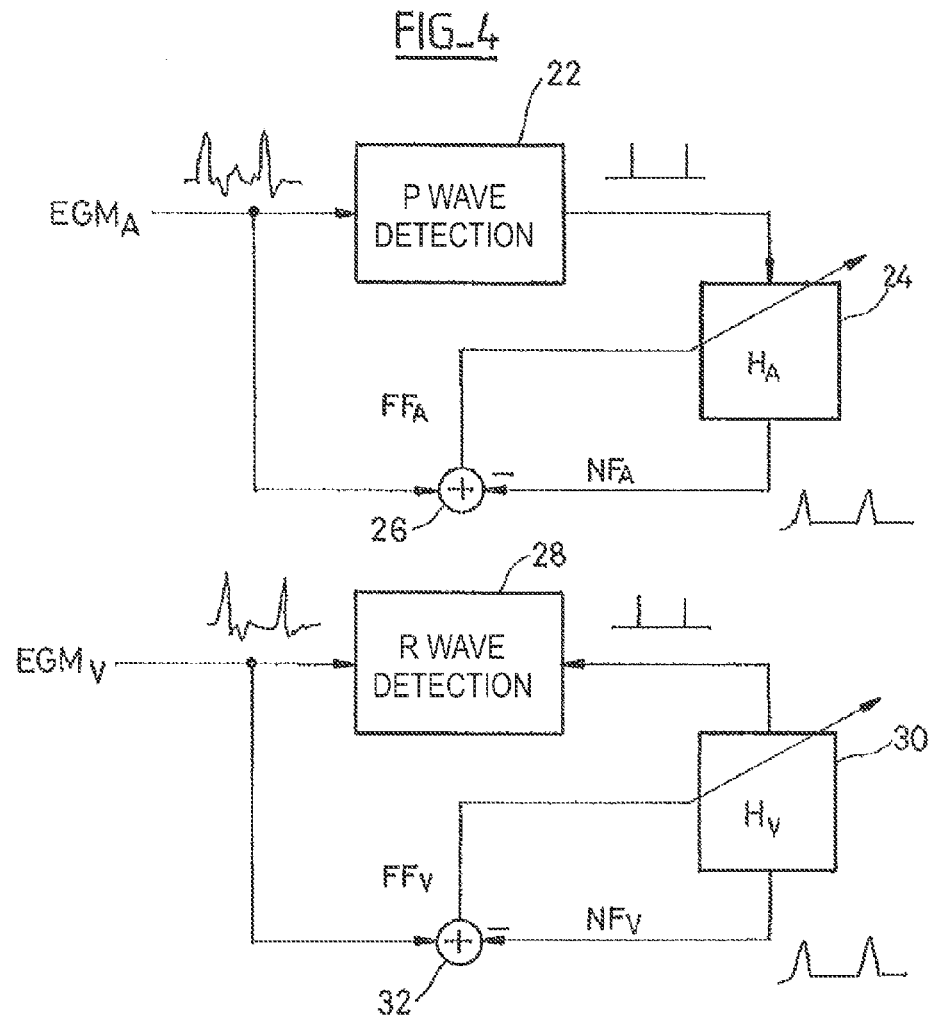
FIG_4
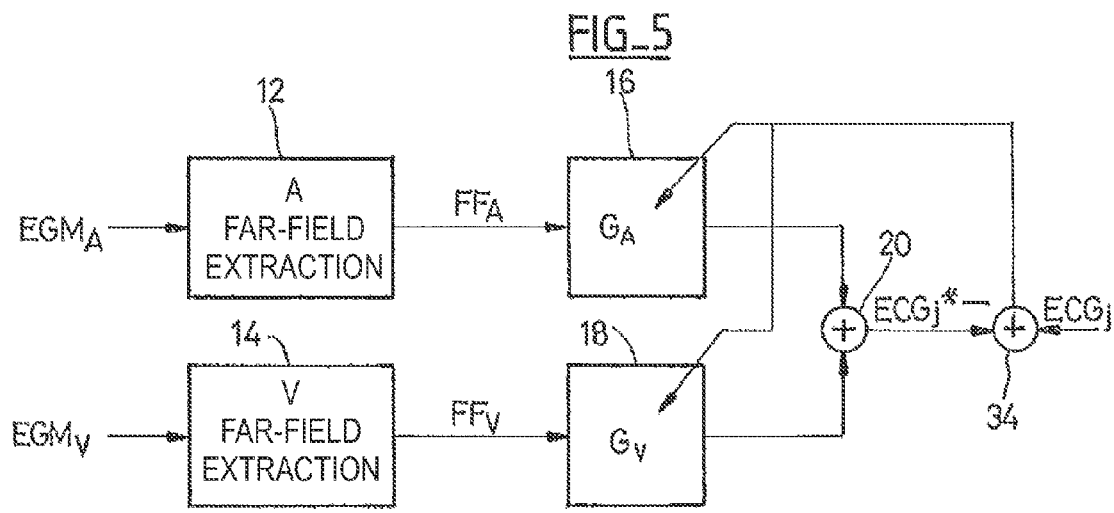
FIG_5

US 8,359,089 B2

RECONSTRUCTION OF A SURFACE ELECTROCARDIOGRAM FROM FAR FIELD SIGNALS EXTRACTED OF AN ENDOCARDIAL ELECTROGRAM

FIELD OF THE INVENTION

The present invention relates to "implantable medical devices" such as those defined by the Jun. 20, 1990 Directive 90/385/EEC of the Council of European Communities, specifically to implantable devices that continuously monitor heart rhythm and deliver to the heart, if necessary, electrical stimulation pulses for cardiac resynchronization and/or defibrillation. The invention more particularly relates to processing the signals representative of cardiac depolarization potentials of the myocardium, such signals being collected through epicardial or endocardial electrodes for pacing, sensing or defibrillation of the right and left atria or ventricles, of these implantable devices.

Even more particularly, the present invention is directed to a method, whether or not implemented in an implanted device, for the reconstruction of a surface electrocardiogram (ECG) from an endocardial or epicardial electrogram (EGM).

BACKGROUND OF THE INVENTION

It is known that EGM signals are collected by use of electrodes placed on endocardial or epicardial leads of a device implanted in a patient. These signals, directly related to the electrical activities of cardiac cells of the patient, provide much useful information for the purpose of assessing the patient's condition. Hence, after amplifying, conditioning, digitizing and filtering, EGM signals are mainly utilized to control the implanted device and diagnose rhythm disorders requiring, for example, automatic triggering of an antitachycardia, antibradycardia, or interventricular resynchronization therapy.

However, when it comes to analyzing subjectively the cardiac rhythm, e.g., to perform a diagnosis or readjust the control/operating parameters of an implanted device, the practitioners prefer, in practice, to interpret the information given by a surface electrocardiogram (ECG). An ECG allows one to visualize in a direct manner, a certain number of determining factors (e.g., QRS width) and thereby assess the evolution of a cardiac failure.

ECG signals are usually recorded over a long period of time through ambulatory practice by Holter recorders. The recorded ECG signals are then further processed and analyzed in order to evaluate the clinical condition of the patient and eventually diagnose whether a cardiac rhythm disorder is present.

The ECG and EGM signals actually have the same signal source (i.e., the electrical activity of myocardium), however, they visually appear in much different manners: the EGM collected by the implantable device provides local information on the electrical activity of a group of heart cells, whereas the ECG appears in the form of more global information, in particular influenced by the propagation of the electrical signals between the myocardium and body surface, with certain morphologic and pathologic specificities. Thus, the display of EGM signals is not very useful to a practitioner who interprets ECG signals.

When a patient implanted with a medical device comes to his practitioner for a routine visit, two distinct devices are used: an ECG recorder and an external implant programmer. In order to collect the ECG signal, the practitioner places electrodes in particular locations relative to the patient's torso. The ECG signals are collected between predefined pairs of electrodes to define typically twelve "derivations" of the collected ECG signals. The external programmer is used to control certain operating parameters of the implantable device (e.g., the battery life), download data from the implantable device memory, modify the parameters thereof, or upload an updated version of the device operating software, etc.

The visit with the practitioner therefore usually requires these two different devices, as well as specific manipulations for placing the surface electrodes and collecting the ECG signals. Moreover, the use of these two devices requires the patient to come to a specifically equipped center, usually having the consequence that routine visits are spaced farther apart, resulting in a less rigorous follow-up of the patient.

Furthermore, the ECG recording has various drawbacks, notably:
- the preparation of the patient which requires a certain time, correlated with a globally increased follow-up cost;
- the local irritation of the skin created by fixing of the electrodes in some patients;
- the position of the electrodes varies from one visit to another, inducing variations in the reconstructed ECG;
- the ECG is affected by several parameters difficult to control, such as breathing, movements of the patient, as well as the interferences emitted by various external electrical sources.

In order to overcome such drawbacks, some algorithms have been developed for reconstruction of the ECG based upon EGM signals that are directly provided by the implantable device. Indeed, reconstruction of the ECG based upon EGM signals would:
- avoid, during routine visits, having to place surface electrodes and resort to an ECG recorder;
- render the visit simpler and quicker, eventually allow performing the routine visit at the patient's home, and subsequently shorten the intervals between successive visits, and improve the patient's follow-up; and
- allow a remote transmission of the EGM data recorded by the implanted device, without the intervention of a practitioner or medical aid.

Various algorithms for surface ECG reconstruction based upon EGM signals have been previously proposed. Certain of the techniques implement a linear or non-linear combination of a plurality of EGM signals.

U.S. Pat. No. 5,740,811 (Hedberg, et al.) proposes to synthesize an ECG signal by combining a plurality of EGM signals by means of a neural network and/or fuzzy logic and/or summer circuit, after a learning process by a "feedforward" type algorithm. Such technique do not take into account the propagation time delay between the EGM signals and the surface ECG signals leading to a precision loss in the reconstructed ECG signal. Another drawback of such technique is that it does not take into account the varying position of the endocardial leads between the moment of the learning process and that of the use of the device; a change in the heart electrical axis may bias the synthesized ECG signal, generating a misleading ECG signal. A cardiac disorder that is masked by the biased synthesis may not be accurately diagnosed.

U.S. Pat. No. 6,980,850 (Kroll et al.) proposes a method of ECG reconstruction by implementing a matrix transform allowing to render each of the surface ECG derivations individually. Such transform also allows to take into account several parameters, such as patient's respiratory activity or posture that influence tracking the position of the endocardial leads through space. The proposed reconstruction consists of transforming, through a predetermined transfer matrix, an input vector representative of a plurality of EGM signals into a resulting vector representative of the different ECG derivations. The transfer matrix is learned through averaging several instantaneous matrices based upon ECG and EGM vectors recorded simultaneously over a same period of time.

Although this technique brings an improvement to that proposed in U.S. Pat. No. 5,740,811, it nevertheless presents certain drawbacks. First, it makes an assumption that there exists a linear relationship between ECG and EGM vectors: such an approximation, though relatively accurate with patients presenting a regular rhythm, leads in some cases to large errors of ECG reconstruction in the presence of atypical or irregular signal morphologies—corresponding to potentially pathologic cases. Second, in the presence of noise, it does not provide a solution for appropriately reconstructing the ECG signals.

The U.S. Pat. No. 7,383,080, the EP 1897587 A2 and the U.S. 2008/0065161 describe yet another technique for concatenating a ventricular far field signal (distant signal) observed on an atrium electrode on one hand, with an atrial far field signal (distant signal) observed on a ventricular electrode on the other hand, to reconstruct an ECG signal. By convention, here and in what follows:

"atrial far field" or $FF_A$ designates a depolarization signal from a ventricular origin (the ventricular distant "electric noise") observed on an electrode placed in the atrium during or just after an occurrence of an R wave, and "ventricular far field" $FF_V$ designates a depolarization signal from an atrial origin (the atrial distant "electric noise") observed on an electrode placed in the ventricle during or just after an occurrence of a P wave.

This known prior art concatenating technique is illustrated in FIG. 1. On this figure, an atrial far field signal $FF_A$ extracted from the atrial EGM signal $EGM_A$ over the duration of a time window surrounding a peak R (spontaneous activity having its origin in the ventricle) is represented, this peak being located on the ventricular EGM signal $EGM_V$. Similarly, a ventricular far field signal $FF_V$ is extracted from the signal $EGM_V$ during a time window surrounding a peak P (spontaneous activity having its origin in the atrium), said peak being located on the atrial EGM signal $EGM_A$.

The reconstructed ECG signal (designated herein as "ECG*") is obtained by concatenating the segments $FF_V$ and $FF_A$ after subtraction of an offset and multiplication of each segment by a given factor of amplification or attenuation, so as to connect these segments between them during their concatenation.

This technique presents a number of advantages:

in the case of a patient with a regular heart rhythm, it is effective because the two far field signals are well separated;

it is simple to implement, and can therefore be implemented in real time within an implanted device;

it does not require the collection of an ECG, unlike methods that use linear or nonlinear EGM signals and require a learning phase for determining the coefficients of filters or of transfer matrices; and it can detect polarity reversals on some ECG signals, while the reconstruction of this polarity reversal is not possible if a linear or nonlinear processing of all EGM signals is performed.

These advantages are however tempered by a number of drawbacks:

for a patient with an irregular heart rhythm, thus potentially pathological illness, far field signals are hidden in P and R waves and cannot be satisfactorily isolated;

the reconstructed "electrocardiogram" signal does not correspond to any real ECG derivation. The technique provides an emulation of a virtual ECG signal ("ECG-like signal"), and is useful for diagnosis, rather than to realistically reconstruct an ECG signal which, ideally, would reproduce a signal collected on one or several derivations of a surface electrocardiogram; and this technique can produce only one type of ECG signal, not a plurality of reconstructed ECG signals, similar to what would be obtained during the collection of a conventional surface electrocardiogram.

These various drawbacks are notably due to the fact the EGM and ECG signals, even if they have the same origin, have very different characteristics. Indeed, the electrical activities of a patient's heart reflect the spontaneous stimulations caused by the ionic currents in the cardiac cells or artificial stimulations produced by the application on an electrical current to these cells. The EGM signals, directly collected by the implant on one or more derivations, reflect the electrical potentials of the myocardium, whereas the ECG signals correspond to the electrical potentials recorded on a body surface, over a certain number of derivations, after propagating from the myocardium.

Another drawback, specific to all these techniques, is that they do not allow verifying that the reconstruction of ECG signals gives a correct result, and do not provide a criterion quantifying the quality of the reconstruction.

It would be desirable to have such a criterion, especially in terms of the intended use of the reconstructed ECG signals: for a simple determination of the presence or absence of a peak, or a QRS complex, the ECG signals are reconstructed with an average quality, while for accurate diagnosis based on specific details of ECG or measurements on this ECG, the ECG signals must be reconstructed with a superior quality.

OBJECT AND SUMMARY OF THE INVENTION

It is therefore an object of the present invention to propose a new reconstruction of ECG signals from EGM signals which, while retaining the advantages of techniques based on a reconstruction from far field signals (including simplicity of the implementation) and overcoming the aforementioned drawbacks. The present teachings described herein, therefore:

is applicable to irregular rhythm situations where far field signals are difficult to distinguish from P and R waves;

produces a reconstructed ECG signal that is as close as possible to an ECG signal collected by a recorder of surface ECG signals;

simultaneously delivers a plurality of reconstructed ECG signals, corresponding to as many different ECG leads.

The device described and claimed herein is of a generic type notably described in the EP 1 897 587 A2 cited above, that processes EGM signals from endocardial or epicardial electrograms representative of a cardiac potential of depolarization of the myocardium and collected on EGM derivations of the device. One such device includes:

means for collecting a ventricular EGM signal ($EGM_V$) and an atrial EGM signal ($EGM_A$);

means for extracting a ventricular far field signal component ($FF_V$) from the collected ventricular EGM signal ($EGM_V$) and an atrial far field signal component ($FF_A$) from the collected atrial EGM signal ($EGM_A$); and means for reconstructing a surface electrocardiogram (ECG) from the ventricular far field signal component and the atrial far field signal component, and delivering an output signal of a reconstructed surface electrocardiogram (ECG*), wherein:

the means for extracting the ventricular far field signal component and the atrial far field signal component comprises, for each of a ventricular derivation and an atrial derivation:

means (22, 28) for detecting a spontaneous or stimulated (P, R) depolarization wave, receiving as an input the EGM signal and delivering as an output a corresponding pulse signal;

a near field estimator filter (24, 30), receiving as an input the pulse signal and delivering as an output a near field signal component ($NF_A$, $NF_V$); and means (26, 32) for subtracting from the EGM signal ($EGM_A$, $EGM_V$) the near field signal component ($NF_A$, $NF_V$) and for delivering as an output said far field signal component ($FF_A$, $FF_V$); and the means for reconstructing an ECG include:

a ventricular far field estimator filter (18), receiving as an input said ventricular far field component signal and delivering as an output a filtered ventricular far field signal component;

an atrial far field estimator filter (16), receiving as input said atrial far field signal component and delivering as an output a filtered atrial far field signal component; and an adder (20) adding the filtered ventricular and atrial far field signal components and delivering as output said reconstructed surface electrocardiogram signal.

Preferably, the device is configured such that the near field estimator filters (24, 30) include a set of parameters ($H_A$, $H_V$) defining a set of filter characteristics, and further comprising means for determining said near field estimator filter parameters ($H_A$, $H_V$), including an adaptive filtering algorithm for iteratively calculating said parameters.

In a preferred embodiment, the far field estimator filters (16, 18) comprise a set of parameters ($G_A$, $G_V$) defining filter characteristics, and the device further comprises means for predetermining the far field estimator filter parameters ($G_A$, $G_V$), comprising:

means for simultaneously collecting a ventricular EGM signal ($EGM_V$), an atrial EGM signal ($EGM_A$), and a surface electrocardiogram signal ($ECG_j$), and means for determining said far field estimator filter parameters ($G_A$, $G_V$) by minimizing a difference ($\epsilon$) between the collected ECG signal (ECG) and a reconstructed ECG signal ($ECG_j^*$).

Preferably, the means for determining the far field estimator filter parameters ($G_A$, $G_V$) comprise an adaptive filtering algorithm and iteratively calculating said parameters.

In yet another embodiment, the device described and claimed herein comprises a means for evaluating a quality of the reconstructed ECG ($ECG_j^*$), comprising:

means for simultaneously collecting a ventricular EGM signal ($EGM_V$), an atrial EGM signal ($EGM_A$), and an ECG signal ($ECG_j$) and means for calculating a correlation coefficient between, on one hand, the collected ECG signal ($ECG_j$) and, on a second hand, a reconstructed ECG signal ($ECG_j^*$) based upon ventricular and atrial far field estimator filters and the atrial and ventricular EGM signals.

More preferable, the device far field estimator filters (16, 18) comprise a set of parameters ($G_A$, $G_V$) defining filter characteristics, and the device further comprises:

means for predetermining the ventricular and atrial far field estimator filters (16, 18) parameters ($G_A$, $G_V$), and means for validating the predetermined parameters by comparing to a given threshold the correlation coefficient calculated by said means for evaluating the quality of reconstruction, and validating or refuting said predetermined parameters depending on the result of the comparison.

In yet another embodiment, the device receives the ventricular and atrial EGM signals ($EGM_A$, $EGM_V$) collected from electrodes selected from the following group: distal and/or proximal right ventricular electrode, distal and/or proximal right atrial electrode, distal and/or proximal left ventricular electrode, coil of ventricular or atrial defibrillation, supra-ventricular defibrillation coil.

The invention can be implemented in various forms. For example, the device may be an implantable cardiac prosthesis device selected from a group of stimulation, resynchronization, cardioversion and defibrillation type devices. Alternatively, the device may be an external programmer comprising means for downloading and analyzing EGM signals collected by an implanted device, or a home monitor, including means for downloading and analyzing EGM signals collected by an implanted device and producing therefrom data, and means for automatic uploading said data to a remote site. In yet another embodiment, the device may be a data server of a site receiving data from a remote monitor for home monitoring including means for downloading EGM signals collected by an implanted device, and means for automatically transmitting said downloaded EGM signals to said remote site.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed, in which like reference characters refer to like elements, and in which:

FIG. 1 schematically presents a prior art technique for reconstructing ECG signals by concatenating far field signals;

FIG. 2 is a schematic representation of the reconstruction technique according to a preferred embodiment of the present invention;

FIG. 3 is a schematic representation of blocks for extracting ventricular and atrial far field signals;

FIG. 4 illustrates an exemplary diagram outlining how the coefficients of the filters of the detection blocks of the far field signals of FIG. 3 are determined; and FIG. 5 illustrates an exemplary diagram explaining how the coefficients of the predictor filters of ECG signal of FIG. 1 are determined by a preliminary learning phase.

DETAILED DESCRIPTION OF THE INVENTION

With reference to the drawings FIGS. 1-5, several examples of implementations of preferred embodiments of the present invention will now be described. Preferably, the functionality and processes of the present invention as described herein can be implemented by an appropriate programming of software of a known implantable pulse generator, for example, a pacemaker or defibrillator/cardioverter, comprising known and conventional circuits and signal acquisition and processing algorithms for acquiring a signal provided through endocardial leads and/or several implanted sensors.

The invention can advantageously be applied to and implemented in the commercial implantable devices marketed by Sorin CRM, Montrouge France, such as the Reply™ and Paradym™ brand pacemakers and comparable commercial and/or proprietary devices of other manufacturers. These devices are equipped with programmable microprocessors, including circuits intended to acquire, condition and process electrical signals collected by implanted electrodes and various sensors, and deliver pacing pulses to implanted electrodes. It is also possible to upload towards these devices, by telemetry, pieces of software (i.e., a software control module) that will be stored in internal memory and run so as to implement the features and functionality of the present invention, as described herein. Implementing the features of the invention into these devices is believed to be easily within the abilities of a person of ordinary skill in the art, and will therefore not be described in detail.

The invention may be implemented within an implant (i.e., direct data processing of the EGM signals by the implanted device), but it may also be implemented in an external programmer used by a practitioner by downloading and analyzing the cardiac signals collected and memorized by an implant.

In yet another advantageous preferred embodiment, the invention is implemented in a home monitor. The home monitor is a special type of programmer whose operation is essentially fully automated without requiring a practitioner. It is particularly intended to allow transmission at regular intervals to a remote site of the collected and analyzed data, e.g. daily, in order to monitor the cardiac condition of the patient remotely.

The invention may also be implemented at a server located at a remote site. For example, the raw EGM data from the implanted device is uploaded to the remote site server directly, without prior processing. The processing is performed by the remote server or a terminal (e.g., a PC computer or programmer) that implements the present invention.

A. Collection of the EGM Signals

In the preferred embodiment, EGM signals are acquired on two "derivations", namely an atrial derivation and a ventricular derivation. Each of these derivations corresponds to a pair of endocardial or epicardial electrodes connected to the housing or CAN of the implanted cardiac prosthesis.

The choice of electrodes defining these derivations depends on the considered cardiac prosthesis: pacemakers (for treatment of bradycardia), defibrillator (for treatment of tachycardia and fibrillation) or resynchronizer (for treatment of heart failure). Three modes of stimulation can also be distinguished: single, double or triple chamber. Different electrodes—and EGM signals which are not the same, as appropriate—correspond to these functions.

As used herein "RV", "RA" and "LV", respectively, designate the right ventricular, right atrial and left ventricular electrodes of the intracardiac leads with a "+" or "−" sign indicating the distal or proximal position of the electrode, and "CoilV" and "SVC" respectively designate the ventricular and supraventricular defibrillation coils. Thus, the possible combinations of electrodes are (with each time, the possibility to select a bipolar configuration by considering the difference between two electrodes or to select an unipolar configuration by considering the difference between one electrode and the generator housing or CAN):

single chamber: RV+, RV− (and CoilV and in the case of a defibrillator), a single chamber pacemaker provides two EGM signals through the distal and proximal electrodes, the ground being taken on the CAN. The version in a defibrillator delivers three EGM signals through the added CoilV electrode.

dual chamber: RV+, RV−, RA+, RA− (and CoilV and SVC in the case of a defibrillator), a dual-chamber pacemaker provides four EGM signals, and six in a defibrillator version.

triple chamber: RV+, RV−, RA+, RA−, LV+, LV− (and CoilV and SVC in the case of a defibrillator), a triple chamber pacemaker provides six EGM signals, and eight in a defibrillator version.

B. Principle of Reconstruction of the ECG

The ECG signals, which are the manifestation of the cardiac electrical activities on the surface of the patient's body, are well known and normally collected between pairs of electrodes applied in predetermined locations of the patient's chest. Each pair of electrodes determines a "derivation". The whole forms a set of twelve derivations, including bipolar derivations (I, II, III), unipolar derivations (aVF, aVR, aVL) and precordial derivations (V1 to V6).

According to one embodiment, the present invention reconstructs one or more of these ECG derivations from signals actually collected on two EGM derivations, namely an atrial derivation (signal $EGM_A$) and a ventricular derivation (signal $EGM_V$).

The basic principle of the reconstruction technique of the invention is described with reference to FIG. 2. An atrial EGM signal $EGM_A$ and a ventricular EGM signal $EGM_V$ are collected according to the method described above for two EGM derivations respectively, and sampled. Each of these signals is respectively applied to a far field signal extraction block 12 (extraction of atrial far field signal $FF_A$) and block 14 (extraction of ventricular far field signal $FF_V$). These far field signals $FF_A$ and $FF_V$ are applied to respective filters 16, 18 that have corresponding linear or nonlinear transfer functions $G_A$, $G_V$. The outputs of filters 16, 18 are summed in adder 20 to produce a reconstructed signal $ECG^*_j$, where j=1, 2 . . . 12 corresponding to the traditional twelve ECG derivations that are to be reconstructed.

For signals collected from other ECG leads that are optionally reconstructed, the same technique is applied with the same $EGM_A$ and $EGM_V$ signals as input, but with different filter parameters $G_A$ and $G_V$.

The $G_A$ and $G_V$ filters may be linear or nonlinear filters such as Volterra filters or neural networks. The Volterra filter is described, for example, by Schetzen M, The Volterra and Wiener Theories of Nonlinear Systems, Wiley and Sons, New York, 1980, or by V J Mathews, "Adaptive Polynomial Filters," IEEE Signal Processing Magazine, 8 (3) pp. 10-26, July 1991. These filters allow in particular establishing between the EGM signals and the ECG signals a non-linear relationship including linear, quadratic and cubic terms. They also introduce in this relationship a finite delay that reflects the propagation time for the electrical signals to propagate through body tissues from the myocardium to the surface of the skin of the patient.

Alternatively, a suitable neural network can perform the expected functions after a learning phase by trying to minimize, in the sense of the least squares method, the mean squared error $\epsilon^2$. A neural network implementing a "time-delay approach" can be used, as described by Hornik K, Stinchcombe M, *Multilayer Feedforward Networks are Universal approximator*, Neural Networks, Vol. 2, No. 5 pp. 359-366, 1989 (for an FTDNN approach, *Focused Time-Delayed Neural Networks*), Elman J L, Finding Structure in Time, Cognitive Science, Vol. 14, pp. 179-211, 1990 (for an approach like Elman), or P Rodriguez, J Wiles and J L Elman,

*A Recurrent Neural Network that Learns to Count*, Connection Science, Vol 11, No. 1, pp. 5-40, 1999 (for a RTDNN type approach, *Recurrent Time-Delayed Neural Networks*).

The structure of the far-field extraction blocks 12, 14 extracting atrial and ventricular signals is described in more details with respect to FIG. 3. The detection blocks 22, 28 detect P wave in the atrial EGM signal $EGM_A$ and R wave in the ventricular EGM signal $EGM_V$, respectively. The detection is done through the use of unmodified, well-known algorithms. The output of the detection blocks 22, 28 is preferably in the form of a series of pulses having positions that indicate the instant of occurrence of the P or R peaks, and an amplitude corresponding to the amplitude of each P or R EGM signal peak.

The signals delivered by the blocks 22, 28 are then applied to respective filters 24, 30 that produce an estimation of a near field atrial signal $NF_A$ and a near field ventricular signal $NF_V$.

As used herein, "$D_P$" denotes the transfer function of block 22 for the detection of the P wave signal from the $EGM_A$ signal, "$D_R$" denotes the transfer function of block 28 for the detection of the R wave from the $EGM_V$ signal, "$H_A$" denotes the transfer function of filter 24 that estimates the atrial near field signal $NF_A$, and "$H_V$" denotes the transfer function of the filter 30 that estimates the ventricular near field signal $NF_V$. Thus, the near field atrial signal $NF_A$ and the near field ventricular signal $NF_V$ are obtained by the following equations:

$$NF_A = H_A(D_P(EGM_A)), \text{ and}$$

$$NF_V = H_V(D_R(EGM_V))$$

$H_A$ and $H_V$ are linear filters and cover a period equal to the width of a QRS complex, or its visible equivalent on the EGM signals. In the case of EGM signals sampled at 128 Hz, the $H_A$ and $H_V$ filters contain approximately 20 to 30 coefficients in order to operate on a time duration of about 140 ms to 250 ms and provide an output pulse response very close to the EGM signal around the P and R peaks.

The far field atrial signal $FF_A$ is obtained by subtracting, at 26, of the atrial near field signal $NF_A$ from the original atrial signal $EGM_A$. The far field ventricular signal $FF_V$ is obtained similarly by subtracting at stage 32 ventricular near field $NF_V$ signal from the original ventricular $EGM_V$ signal, that is:

$$FF_A = EGM_A - NF_A \text{ and}$$

$$FF_V = EGM_V - NF_V.$$

The coefficients of the $H_A$ and $H_V$ filters (blocks 24 and 30 in FIG. 3) are obtained by a learning phase technique for the form of the P and R waves, as shown in FIG. 4. This learning phase implements an adaptive filtering, active only during the time intervals containing well separated P and R peaks. The filters cover the duration of a QRS complex, and the learning phase takes place over several cardiac cycles, comparing at adder (26) the atrial near field signal $NF_A$ resulting from the estimation by the block channel 24 with the original signal $EGM_A$, and, similarly, comparing at adder stage 32 the ventricular near field signal $NF_V$, resulting from the estimation by the block channel 30, with the original signal $EGM_V$.

The error signals denoted by the far field signals $FF_A$ and $FF_V$, control by a known technique the adaptation of the filter $H_A$ (or $H_V$). For example, the adaptation occurs through an algorithm of the adaptive least mean squares LMS type or, advantageously, an algorithm implementing the method of the recursive least squares RLS. The RLS method is described, for example, by Hayes, M H (1996), Recursive Least Squares, *Statistical Digital Signal Processing and Modeling*, Wiley, p. 541 (ISBN 0-471-59431-8), or by S Haykin, *Adaptive Filter Theory*, Prentice Hall, 2002 (ISBN 0-13-048434-2). It solves a linear system in real-time and requires less computational resources for calculating coefficients than matrix inversion, so it can be implemented directly in an implantable device without an external programmer. Also, the use of a variable step to control the convergence of the iterations has an advantage as compared to iterative methods with a fixed step as is used in the LMS method.

It should be understood that the learning phase of the filters $H_A$ and $H_V$ does not require prior collection of an ECG signal. According to one embodiment, this learning phase operates in closed loop, continuously, or in open loop after a periodic learning phase or following a predetermined event.

The method of determination of the coefficients of the reconstruction filters $G_A$ and $G_V$ (blocks 16 and 18 of FIG. 2) is described with reference to FIG. 5. The coefficients of the filters $G_A$ and $G_V$ that provide a reconstructed surface electrocardiogram signal $ECG^*_j$ from the atrial far field signal $FF_A$ and the ventricular far field signal $FF_V$ are determined by learning the form of the ECG signals. The learning phase is operated in a first phase by simultaneously collecting a set of reference data consisting of the atrial electrogram signal $EGM_A$ and the ventricular electrogram signal $EGM_V$ and of surface electrocardiogram signals $ECG_j$ synchronized with these EGM signals.

The filters $G_A$ and $G_V$ as noted above, may be linear or nonlinear filters, for example, Volterra filters or neural networks. Preferably, both the $G_A$ and $G_V$ filters corresponding to each derivation j are calculated. The coefficients of the filters $G_A$ and $G_V$ depend on: (i) the patient, (ii) the EGM signals used as input for the reconstruction, and (iii) the ECG derivation that is to be reconstructed.

To do this, a reconstructed ECG $ECG^*_j$ is estimated from the $EGM_A$ and $EGM_V$ signals by the technique described above with reference to FIG. 2—extraction of far field signals by blocks 12, 14, and estimation of ECG by blocks 16, 18, respectively. The difference between the real ECG $ECG_j$ and the reconstructed ECG $ECG^*_j$ is evaluated at adder stage 34. The difference signal controls the adaptive filters $G_A$ and $G_V$ according to known adaptation schemes such as LMS, RLS (described above with reference to the adaptive filters $H_A$ and $H_V$ in FIG. 4), or any other learning technique.

Once the coefficients of the $G_A$ and $G_V$ filters are adapted and determined, the filters $G_A$ and $G_V$ are operating in an open-loop mode in order to reconstruct in real time, an $ECG^*_j$ derivation, in the manner described with reference to FIG. 2.

C. Assessment of the Quality of the Reconstruction of the ECG.

Another aspect of the present invention is directed to an assessment of a quality of the ECG reconstruction. It is indeed interesting to estimate the quality of the reconstruction, for example, to choose a particular reconstruction technique based on an acceptable compromise between the device constraints (e.g., computation time, hardware and software resources available) and the expected use of the reconstructed ECG (e.g., detection of the mere presence of certain characteristics, or otherwise further examination of the waveforms).

To assess a quality of the reconstruction, the EGM and actual ECG signals are acquired simultaneously during a period of measurement $T_m$. The period $T_m$ represents at least two cardiac cycles (approximately 2 seconds) and up to 100 or 1000 seconds. The sequences chosen as a reference data set for the learning phase has a duration $T_r$ of at least one second and can be as large as 99 or 999 seconds. The EGM and ECG signals are acquired simultaneously during a period $T_m$, typically with a sampling rate of 128 Hz.

If the sampling frequency of the ECG and EGM signals (usually located in the range 100 Hz to 1 kHz) are different, the data is synchronized by a suitable technique, such as interpolation (e.g., linear, polynomial or by splines) or compression (e.g., the Mueller turning point algorithm), as would be understood by a person of ordinary skill in the art.

The quality of the reconstruction of ECG signals is evaluated by a numerical criterion consisting of determining, on a sequence that has not been used for the learning phase, the coefficient of correlation $\rho$ between the real ECG signals $y[k]$ and the reconstructed ECG signals $y_{rec}[k]$.

Specifically, a time delay shift of the order of 40 ms (i.e., a shift of d=5 samples for a sampling frequency of 128 Hz) in the reconstructed signal does not alter the diagnostic capabilities of the sampled ECG signals.

The correlation coefficient is estimated for each shift k:

$$\rho_k = \frac{\sum_{i=0}^{J}(y[i]-\bar{y})(y_{rec}[i+k]-\bar{y}_{rec})}{\sqrt{\sum_{i=0}^{J}(y[i]-\bar{y})^2}\sqrt{\sum_{i=0}^{J}(y_{rec}[i+k]-\bar{y}_{rec})^2}}$$

The quality of reconstruction (between $-1$ and $+1$) is estimated by $$\rho = \max_{-d \le k \le d}(\rho_k)$$

For ECG sequences that have a regular heart rhythm, the present invention provides a reconstruction quality that is greater than 80% from unipolar signals from the atrium and ventricle (the proximal signal being considered in reference to the housing or CAN). The reconstructed ECG signals advantageously faithfully reproduce the polarity, width and position of the QRS complex.

In some patients with an irregular heart rhythm, the present invention provides a reconstruction quality of about 70% to 75% on certain ECG sequences, while the other methods based on direct processing of the EGM without far field extraction provide a reconstruction quality of less than 50%.

Specifically, the quality of reconstruction must be on the order of at least 60 to 65% to be capable to trace in the reconstructed ECG some peculiarities that we look to determine its presence or absence such as peaks and QRS complexes. These peculiarities may be sufficient for a quick patient follow-up visit for ECG monitoring. However, in order to establish a more accurate diagnosis from a detailed examination of the waveforms, the quality of reconstruction must be at least about 80%.

Advantageously, the criterion of reconstruction quality is especially used to validate the calculation of the filter coefficients during the learning process. Thus, after calculating the filter settings, the reconstruction quality is compared to a threshold. This threshold is programmable and may possibly be modified by the practitioner, or may be preset to an acceptable value, say 60%.

If the quality criterion is verified (i.e., threshold is exceeded), the estimated coefficients are stored and used for the filters in calculating the subsequent ECG derivation reconstructions. The process is optionally repeated for each ECG derivation to be reconstructed.

However, if the criterion is not verified, it is necessary to restart the determination of the filter settings, either by selecting a different reference period $T_r$ in the measurement window $T_m$ (e.g., in the window $T_r$, arrhythmias may be present that might interfere with the learning process), or by repeating the acquisition of another data set over another duration $T_m$.

One skilled in the art will appreciate that the present invention can be protected by embodiments other than those described herein, which are provided for purposes of illustration and not of limitation.

I claim:

1. A device for processing signals representative of a cardiac potential of depolarization of the myocardium, comprising:
   means for collecting a ventricular EGM signal ($EGM_V$) and an atrial EGM signal ($EGM_A$);
   means for extracting a ventricular far field signal component ($FF_V$) from the collected ventricular EGM signal ($EGM_V$) and an atrial far field, signal component ($FF_A$) from the collected atrial EGM signal ($EGM_A$); and
   means for reconstructing a surface electrocardiogram (ECG) from the ventricular far field signal component and the atrial far field signal component, and delivering an output signal of a reconstructed surface electrocardiogram ($ECG_j^*$), wherein:
   the means for extracting the ventricular far field signal component and the atrial far field signal component comprises, for each of a ventricular derivation and an atrial derivation:
      means (22, 28) for detecting a spontaneous or stimulated (P, R) depolarization wave, receiving as an input the EGM signal and delivering as an output a corresponding pulse signal;
      a near field estimator filter (24, 30), receiving as an input the pulse signal and delivering as an output a near field signal component ($NF_A$, $NF_V$); and
      means (26, 32) for subtracting from the EGM signal ($EGM_A$, $EGM_V$) the near field signal component ($NF_A$, $NF_V$) and for delivering as an output said far field signal component ($FF_A$, $FF_V$); and
   the means for reconstructing an ECG include:
      a ventricular far field estimator filter (18), receiving as an input, said ventricular far field component signal and delivering as an output a filtered ventricular far field signal component;
      an atrial far field estimator filter (16), receiving as input said atrial far field signal component and delivering as an output a filtered atrial far field signal component; and
      an adder (20) adding the filtered ventricular and atrial far field signal components and delivering as output said reconstructed surface electrocardiogram signal.

2. The device of claim 1, wherein the near field estimator filters (24, 30) comprise a set of parameters ($H_A$, $H_V$) defining a set of filter characteristics, and further comprises means for determining said near field estimator filter parameters ($H_A$, $H_V$) through an adaptive filtering algorithm for iteratively calculating said parameters.

3. The device of claim 1, wherein the far field estimator filters (16, 18) comprise a set of parameters ($G_A$, $G_V$) defining filter characteristics, and further comprises means for predetermining the far field estimator filter parameters ($G_A$, $G_V$), comprising:
   means for simultaneously collecting a ventricular EGM signal ($EGM_V$), an atrial EGM signal ($EGM_A$), and a surface electrocardiogram signal ($ECG_j$), and means for determining said far field estimator filter parameters ($G_A$, $G_V$) by minimizing a difference ($\epsilon$) between the collected ECG signal ($ECG_j$) and a reconstructed ECG signal ($ECG_j^*$).

4. The device of claim 3, wherein the means for determining the far field estimator filter parameters ($G_A$, $G_V$) comprises an adaptive filtering algorithm and iteratively calculating the parameters.

5. The device of claim 1, further comprising means for evaluating a quality of the reconstructed ECG ($ECG_j^*$), comprising:
means for simultaneously collecting a ventricular EGM signal ($EGM_V$), an atrial EGM signal ($EGM_A$), and an ECG signal ($ECG_j$) and
means for calculating a correlation coefficient between, on one hand, the collected ECG signal ($ECG_j$) and, on a second hand, a reconstructed ECG signal ($ECG_j^*$) based upon ventricular and atrial far field estimator filters and the atrial and ventricular EGM signals.

6. The device of claim 5, wherein the far field estimator filters (16, 18) comprise a set of parameters ($G_A$, $G_V$) defining filter characteristics, and further comprises:
means for predetermining the ventricular and atrial far field estimator filters (16, 18) parameters ($G_A$, $G_V$), and
means for validating the predetermined parameters by comparing to a given threshold the correlation coefficient calculated by said means for evaluating the quality of reconstruction, and validating or refuting said predetermined parameters depending on the result of the comparison.

7. The device of claim 1, wherein the device receives the ventricular and atrial EGM signals ($EGV_A$, $EGM_V$) collected from electrodes selected from a group of distal and/or proximal right ventricular electrode, distal and/or proximal right atrial electrode, distal and/or proximal left ventricular electrode, coil of ventricular or atrial defibrillation, supra-ventricular defibrillation coil.

8. The device of claim 1, wherein said device is an implantable cardiac prosthesis device selected from a group of stimulation, resynchronization, cardioversion and defibrillation type.

9. The device of claim 1, wherein said device is an external programmer comprising means for downloading and analyzing EGM signals collected by an implant.

10. The device of claim 1, wherein said device is a home monitor, including means for downloading and analyzing EGM signals collected by an implant and producing therefrom data, and means for automatic uploading said data to a remote site.

11. The device of claim 1, wherein said device is a data server of a site receiving data from a remote monitor for home monitoring including means for downloading EGM signals collected by an implant, and means for automatically transmitting said downloaded EGM signals to said remote site.

12. A device for processing signals representative of a cardiac potential of depolarization of the myocardium, comprising:
means for collecting a ventricular EGM signal ($EGM_V$) and an atrial EGM signal ($EGM_A$);
means for extracting a ventricular far field signal component ($FF_V$) from the collected ventricular EGM signal ($EGM_V$) and an atrial far field signal component ($FF_A$) from the collected atrial EGM signal ($EGM_A$); and
means for reconstructing a surface electrocardiogram (ECG), from the ventricular far field signal component and the atrial far field signal component, and delivering an output signal of a reconstructed surface electrocardiogram ($ECG_j^*$), wherein:
the means for extracting the ventricular far field signal component and the atrial far field signal component comprises, for each of a ventricular derivation and an atrial derivation:
means (22, 28) for detecting a spontaneous or stimulated (P, R) depolarization wave, receiving as an input the EGM signal, and delivering as an output a corresponding pulse signal;
near field estimator filter (24, 30), receiving as an input the pulse signal and delivering as an output a near field signal component ($NF_A$, $NF_V$); and
means (26, 32) for subtracting from the EGM signal ($EGM_A$, $EGM_V$) the near field signal component ($NF_A$, $NF_V$) and for delivering as an output said far field signal component ($FF_A$, $FF_V$); and
the means for reconstructing an ECG include:
a ventricular far field estimator filter (18), receiving as an input said ventricular far field component signal and delivering as an output a filtered ventricular far field signal component;
an atrial far field estimator filter (16), receiving as input said atrial far field signal component and delivering as an output a filtered atrial far field signal component;
an adder (20) adding the filtered ventricular and atrial far field signal components and delivering as output said reconstructed surface electrocardiogram signal; and
wherein the near field estimator filter, ventricular far field estimator filter and atrial far field estimator filter are adaptive implementing a learning phase.

13. The device of claim 12, wherein the near field estimator filters (24, 30) comprise a set of parameters ($H_A$, $H_V$) defining a set of filter characteristics, and further comprises means for determining said near field estimator filter parameters ($H_A$, $H_V$) through an adaptive filtering algorithm for iteratively calculating said parameters.

14. The device of claim 12, wherein the far field estimator filters (16, 18) comprise a set of parameters ($G_A$, $G_V$) defining filter characteristics, and further comprises means for predetermining the far field estimator filter parameters ($G_A$, $G_V$), comprising:
means for simultaneously collecting a ventricular EGM signal ($EGM_V$), an atrial EGM signal ($EGM_A$), and a surface electrocardiogram signal ($ECG_j$), and
means for determining said far field estimator filter parameters ($G_A$, $G_V$) by minimizing a difference ($\epsilon$) between the collected ECG signal ($ECG_j$) and a reconstructed ECG signal ($ECG_j^*$).

15. The device of claim 14, wherein the means for determining the far field estimator filter parameters ($G_A$, $G_V$) comprises an adaptive filtering algorithm and iteratively calculating the parameters.

16. The device of claim 12, further comprising means for evaluating a quality of the reconstructed ECG ($ECG_j^*$), comprising:
means for simultaneously collecting a ventricular EGM signal ($EGM_V$), an atrial EGM signal ($EGM_A$), and an ECG signal ($ECG_j$) and
means for calculating a correlation coefficient between, on one hand, the collected ECG signal ($ECG_j$) and, on a second hand, a reconstructed ECG Signal ($ECG_j^*$) based upon ventricular and atrial far field estimator filters and the atrial and ventricular EGM signals.

17. The device, of claim 16, wherein the far field estimator filters (16, 18) comprise a set of parameters ($G_A$, $G_V$) defining filter characteristics, and further comprises:
   means for predetermining the ventricular and atrial far field estimator filters (16, 18) parameters ($G_A$, $G_V$), and
   means for validating the predetermined parameters by comparing to a given threshold the correlation coefficient calculated by said means for evaluating the quality of reconstruction, and validating or refuting said predetermined parameters depending on the result of the comparison.

18. The device of claim 12, wherein the device receives the ventricular and atrial EGM signals ($EGM_A$, $EGM_V$) collected from electrodes selected from a group of distal and/or proximal right ventricular electrode, distal and/or proximal right atrial electrode, distal and/or proximal left ventricular electrode, coil of ventricular or atrial defibrillation, supra-ventricular defibrillation coil.

19. The device of claim 12, wherein said device is an implantable cardiac prosthesis device selected from a group of stimulation, resynchronization, cardioversion and defibrillation type.

20. The device of claim 12, wherein said device is an external programmer comprising means for downloading and analyzing EGM signals collected by an implant.

21. The device of claim 12, wherein said device is a home monitor including means for downloading and analyzing EGM signals collected by an implant and producing therefrom data, and means for automatic uploading said data to a remote site.

22. The device of claim 12, wherein said device is a data server of a site receiving data from a remote monitor for home monitoring including means for downloading EGM signals collected by an implant, and means for automatically transmitting said downloaded EGM signals to said remote site.

* * * * *